United States Patent [19]
Guerrero et al.

[11] Patent Number: 5,741,497
[45] Date of Patent: Apr. 21, 1998

[54] SKIN TREATMENT WITH SALICYLIC ACID ESTERS

[75] Inventors: Angel Augusto Guerrero, Huntington; Peter Ladislaus Dorogi, Norwalk; Thomas Charles Klepacky, Shelton, all of Conn.

[73] Assignee: Elizabeth Arden Company, New York, N.Y.

[21] Appl. No.: 670,390

[22] Filed: Jun. 25, 1996

[51] Int. Cl.$^6$ ............................................. A61K 7/48
[52] U.S. Cl. ................. 424/401; 424/59; 514/844; 514/845; 514/846; 514/847
[58] Field of Search ............... 424/401, 59; 514/844–847

[56] References Cited

U.S. PATENT DOCUMENTS

| | | | |
|---|---|---|---|
| 4,891,227 | 1/1990 | Thaman et al. | 424/443 |
| 4,891,228 | 1/1990 | Thaman et al. | 424/443 |
| 5,262,407 | 11/1993 | Leveque et al. | 514/159 |

FOREIGN PATENT DOCUMENTS

| | | |
|---|---|---|
| 0 713 696 | 10/1994 | European Pat. Off. . |
| 0676194 | 3/1995 | European Pat. Off. . |
| 0 676 194 | 10/1995 | European Pat. Off. . |
| 4 036 238 | of 0000 | Japan . |
| 93/10755 | 6/1993 | WIPO . |
| 93/10756 | 6/1993 | WIPO . |

OTHER PUBLICATIONS

Journal of Investigative Dermatology, Inc., pp. 359–556 (1995) "Application of Retinol to Human Skin In Vivo Induces Epidermal Hyperplasia and Cellular Retinoid Binding Proteins Characteristic of Retinoic Acid but Without Measurable Retinoic Acid Levels or Irritaton".

Elizabeth Arden "SPA Comeback Cream"—(1994) carton with ingredient listing including tridecyl salicylate.

*Primary Examiner*—Jyothsan Venkat
*Attorney, Agent, or Firm*—Milton L. Honig

[57] ABSTRACT

A method and composition is provided for treating skin conditions including those arising from dermatologic disorders, chronoaging and environmental abuse. Non-ring esterified $C_{11}$–$C_{30}$ alkyl or alkenyl esters of salicylic acid are used as the active component in combination with a pharmaceutically acceptable carrier. Most preferred is tridecyl salicylate.

1 Claim, No Drawings

SKIN TREATMENT WITH SALICYLIC ACID ESTERS

BACKGROUND OF THE INVENTION

1. Field of the Invention

The present invention concerns methods of treating skin with compositions containing certain esters of salicylic acid.

2. The Related Art

Skin is subject to deterioration through dermatologic disorders or normal aging (chronoaging) as well as extrinsic factors (environmental). Dermatologic disorders include such conditions as acne, dry skin, dandruff, keratosis, pruritus, inflammatory dermatoses, eczema, psoriasis and tenia pedis (athlete's foot).

Chronoaging results in the thinning and general degradation of skin. As skin naturally ages, there is reduction in the cells and blood vessels that supply the skin. There is also a flattening of the dermal-epidermal junction which results in weaker mechanical resistance. Older individuals increasingly develop facial fine lines, wrinkles, leatheriness, yellowing, sagging, mottling (hyperpigmentation), age spots and the general signs of aging.

Extrinsic factors are primarily those caused by exposure to sun. Changes are most prominent in light skinned individuals who burn easily and tan poorly. The results of photodamage may be identical to those of aging except appearing at an accelerated rate. Wrinkling, yellowing, leatheriness, mottling and hyperpigmentation are all associated with sun damage. Most disturbing to many individuals is the wrinkling effect. It is a prime reminder of the disappearance of youth. As a result, there have been many reports of cosmetic treatments aimed at the elimination of wrinkles.

PCT applications WO 93/10755 and WO 93/10756 report salicylic acid as an effective anti-wrinkling agent. U.S. Pat. No. 5,262,407 reports use of ring acylated salicylic acid as a treatment against skin aging. Salicylic acid has also been described for the treatment of acne in U.S. Pat. No. 4,891,227 and U.S. Pat. No. 4,891,228. Moreover, salicylic acid has been used for the removal of warts, corns and calluses; for the treatment of psoriasis, seborrheic dermatitis and dandruff; and for the topical treatment of ringworm infection. A listing of commercially available products containing salicylic acid will be found in the Physician's Desk Reference, 45th Edition, 1991, page 323.

Ring alkylated salicylic acid has been reported in Japanese Patent 4036238 (Takasago Perfumery KK) for treatment of acne vulgaris.

Significant irritation is often associated with the use of salicylic acid. Another problem is that salicylic acid is not always readily formulatable into oily compositions. Derivatives of salicylic acid most often leave the acidic function free. Irritation caused by acidity is therefore not prevented by such derivatives.

Accordingly it is an object of the present invention to provide a treatment for a variety of dermatologic disorders such as acne, dry skin, dandruff, keratosis, pruritus, inflammatory dermatosis, eczema, psoriasis and tinea pedis.

Another object of the present invention is to provide a treatment for chronoaging conditions including wrinkling and fine lines, leatheriness, yellowing, sagging, mottling (hyperpigmentation), age spots and the general signs of aging.

Still another object of the present invention is to provide a treatment against environmental abuse to skin including wrinkling and fine lines, yellowing, leatheriness, mottling and hyperpigmentation.

Yet another object of the present invention is to provide a treatment to improve the condition of skin with a composition and active that does not impart irritation.

These and other objects of the present invention will become more readily apparent from the following summary and detailed discussion.

SUMMARY OF THE INVENTION

A method is provided for treating skin conditions selected from the group consisting of dermatologic skin disorders, chronoaging, environmental abuse and combinations thereof, by applying to the skin a composition including as an active a salicylate ester having the structure (I):

wherein R is a $C_{11}$–$C_{30}$ alkyl or alkenyl radical.

DETAILED DESCRIPTION OF THE INVENTION

Now it has been discovered that deterioration of skin through dermatologic disorders, chronoaging and environmental abuse (e.g. sun and wind) can be reduced, inhibited and even reversed through application of a cosmetic composition including as active a non-ring ester derivative of salicylic acid having formula (I):

wherein R is a $C_{11}$–$C_{30}$ alkyl or alkenyl radical. Most preferred are the $C_{12}$–$C_{20}$ alkyl or alkenyl, optimally the $C_{13}$ alkyl or alkenyl esters of salicylic acid.

"Safe and effective amounts" of the $C_{11}$–$C_{30}$ esters of salicylic acid are to be used within cosmetic compositions of the present invention. The term "safe and effective amounts" are defined as any amount sufficient to significantly induce a positive modification in the condition to be treated, but low enough to avoid serious side effects (at a reasonable benefit/risk ratio), within the scope of sound medical judgement. The safe and effective amount of the salicylate esters will vary with the particular condition being treated, the age and physical condition of the patient being treated, the severity of the condition, the duration of the treatment, the nature of concurrent therapy, the specific ester employed, the particular pharmaceutically-acceptable carrier utilized, and like factors in the knowledge and expertise of the attending physician. Generally these amounts may range from 0.01 to 20%, preferably from 0.1 to 10%, more preferably from 1 to 8%, optimally from 2 to 6% by weight.

Besides the active salicylate ester, compositions of the present invention will utilize a pharmaceutically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention.

Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as pharmaceutically acceptable carriers. These may be in the form of silicone oils and synthetic esters. Amounts of the emollients may range anywhere from 0.1 to 30%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

The most preferred esters are isoarachidyl neopentanoate and isononyl isononanoate.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the pharmaceutically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include emulsified systems such as lotions and creams, microemulsions, roll-on formulations, mousses, ointments (hydrophilic and hydrophobic), aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_5$, Vitamin $B_6$, Vitamin C and Biotin. One source for Vitamin C is a product sold under the trademark of Vitazyme C available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2$-$C_{25}$ α-hydroxy alkanoic acids may also be incorporated into compositions of this invention. Illustrative of this group of materials are glycolic, lactic, α-hydroxyoctanoic acids and salts thereof. The salts may be selected from alkalimetal, ammonium and $C_1$-$C_{20}$ alkyl or alkanolammonium counterions. Levels of α-hydroxyalkanoic acids may range from 0.001 to 10%, preferably between 0.2 and 1%, optimally between 0.4 and 0.5% by weight.

Minor adjunct ingredients may also be present in the cosmetic compositions. Among them may be the water-insoluble vitamins such as Vitamin A Palmitate, Vitamin E Acetate and DL-panthenol.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont.

Colorants, fragrances, opacifiers and abrasives may also be included in compositions of the present invention. Each of these substances may range from about 0.05 to about 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

The following sunscreen creme was prepared having a composition indicated under Table I.

TABLE I

| COMPONENT | WEIGHT % |
|---|---|
| Carbopol 1382 ® (2% solids) | 8.000 |
| Cyclomethicone | 6.000 |
| Parsol MCX ® | 6.000 |
| Isoarachidyl Neopentanoate | 4.300 |
| Benzophenone-3 | 3.000 |
| Glycerin | 3.000 |
| Isononyl Isononanoate | 2.500 |
| Arlacel 165 VS ® (GMS/PEG) | 1.700 |
| BRIJ 721 ® (Vegetable) | 1.200 |
| Isostearic Acid | 1.200 |
| Polymethyl Methacrylate | 1.000 |
| Cetyl Alcohol | 1.000 |
| Triethanolamine | 0.770 |
| Phenoxyethanol | 0.700 |
| Actiglyde-J Special ® (Bio-hyaluronic acid) | 0.500 |
| Vitamin E Acetate | 0.500 |
| BRIJ 72 ® (Vegetable) | 0.300 |
| Methylparaben | 0.300 |
| Polyethylene (A-C 400) ® | 0.300 |
| Algae Extract | 0.250 |
| Glydant ® | 0.200 |
| DL-Panthenol | 0.200 |
| $C_{12}$-$C_{20}$ Acid-PEG 8 Esters | 0.200 |
| Trilaureth-4-Phosphate | 0.200 |
| Silicone 200 (10 cst) | 0.200 |
| Microat SF ® | 0.200 |
| Niacin | 0.200 |
| Amigel ® | 0.170 |
| Vitazyme C ® | 0.100 |
| Superoxide Dismutase | 0.100 |
| Vitamin $B_6$ | 0.100 |
| Vitamin A Palmitate | 0.100 |
| Propylparaben | 0.100 |
| Disodium EDTA | 0.100 |
| L-Lactic Acid | 0.010 |
| Biotin | 0.001 |
| Deionized Water | qs |

EXAMPLE 2

A creme was prepared having a composition described in Table II.

TABLE II

| COMPONENT | WEIGHT % |
|---|---|
| Carbopol 1382 ® (2% Solids) | 18.000 |
| Cyclomethicone | 6.000 |
| Cetyl Alcohol | 4.400 |
| Spectron SA-13 ® (Tridecyl Salicylate) | 4.000 |
| Glycerin | 3.000 |
| Isoarachidyl Neopentanoate | 2.400 |
| Emulgade 100 NI ® | 1.750 |
| Willowbark Extract | 1.500 |
| Triethanolamine 99% | 1.420 |
| $C_{18}$-$C_{36}$ Fatty Acid | 1.200 |
| BRIJ 721 ® (Vegetable) | 1.200 |
| Arachidyl Behenate | 1.000 |
| Actiglyde-J Special ® | 1.000 |
| Polymethyl Methacrylate | 1.000 |
| Vitamin E Acetate | 1.000 |
| Sodium Pyrolidone Carboxylate (50% solids) | 0.750 |
| Algae Extract | 0.500 |
| DL-Panthenol | 0.500 |
| Silicone 200 (10 cst) | 0.400 |
| $C_{12}$-$C_{20}$ Acid-PEG 8 Esters | 0.400 |
| Microat SF ® | 0360 |
| Bernel Ester TOC ® | 0.360 |
| Glydant ® | 0.300 |
| Methylparaben | 0.300 |
| BRIJ 72 ® (Vegetable) | 0.300 |
| Polyethylene (A-C 400) ® | 0.300 |

TABLE II-continued

| COMPONENT | WEIGHT % |
|---|---|
| Shea Butter | 0.200 |
| Disodium EDTA | 0.100 |
| Amigel ® | 0.100 |
| Propylparaben | 0.100 |
| Vitamin A Acetate | 0.100 |
| L-Lactic Acid | 0.010 |
| Biotin | 0.001 |
| Vitazyme C ® | 0.001 |
| Deionized Water | qs |

EXAMPLE 3

A clinical study was performed on the compositions of Examples 1 and 2. The objective of this study was to evaluate the dermatologic irritation and acnegenic potential of these two compositions when used under exaggerated conditions for twenty-eight days. The study was a monadic treatment type study. The test panel was comprised of 45 female human volunteer subjects (21 using Example 1 and 24 using Example 2). Enrolled subjects had a facial acne grade of II (Pilsbury) or lower and no facial irritation beyond the specific acne lesions.

On days 1, 8, 15 and 29 the investigator assessed the global facial irritation and acne condition of each subject. The lighting conditions, fluorescent overhead lights in a fluorescent ring lamp with a diopter lens (as needed) were identical for each evaluation. Each subject used either product twice daily (morning and evening) for twenty-eight days, recording all use on a diary form.

The investigator's global facial assessments of open lesions, closed lesions, papules, pustules, nodules and irritation were transferred via data entry from the original data sheets to computer. Analysis was conducted using the paired sample t-Test on the global mean scores within each product group and on the differences from baseline in global mean scores for a product vs. product comparison. Significance was assessed at the $p \leq 0.05$ level (95% confidence). Pustules, nodules and irritation scores were negative (0) at all time points. There were no significant increases in any acne condition or irritation at any time point during the study. At week 1 open lesions for Example 2 decreased significantly (p=0.036). At week 4 open lesions decreased for Example 2 and increased for Example 1 indicating a significant difference (p=0.018). At every time point Example 2 demonstrated a decrease in open lesions, closed lesions, and papules. The same conditions worsened at 5 of 9 time points for Example 1. When used as directed, neither product was an irritant.

Although the compositions of Example 1 and 2 vary slightly, the major difference is the presence of 4% tridecyl salicylate in Example 2. From the above study, it is evident that the tridecyl salicylate had a significant effect upon treating the conditions of acne while being nonirritating.

EXAMPLE 4

A microemulsion formulation according to the present invention is outlined under Table III.

TABLE III

| INGREDIENT | WEIGHT (%) |
|---|---|
| PPG-5-Ceteth-20 | 4.00 |
| PEG-40 Hydrogenated Castor Oil | 1.75 |
| Polyglyceryl-10 Decaoleate | 10.50 |
| PEG-8 Caprylic/capric Glycerides | 10.50 |
| SD Alcohol 40 | 12.00 |
| Isodecyl Neopentanoate | 16.00 |
| Glyceryl Trioctanoate | 8.00 |
| DC Silicone Fluid 344 ® | 8.50 |
| Propylparaben | 0.15 |
| Isostearic Acid | 2.50 |
| Tridecyl Salicylate | 3.75 |
| Hydroxycaprilic Acid | 0.10 |
| Tocopheryl Acetate | 0.25 |
| Phenoxyethanol | 0.30 |
| Deionized Water | Q.S |

EXAMPLE 5

A skin lotion (water in oil type) formulation according to the present invention is outlined under Table IV.

TABLE IV

| INGREDIENT | WEIGHT (%) |
|---|---|
| Cetyl Dimethicone | 2.50 |
| DC Silicone Fluid 344 ® | 4.00 |
| DC Silicone Fluid 200 ®(20 CST) | 1.25 |
| Squalane | 1.75 |
| Octyl Octanoate | 2.00 |
| Zinc Myristate | 1.25 |
| Dimethicone Copolyol | 2.50 |
| Butylene Glycol | 4.50 |
| Glycerin | 1.50 |
| Sodium Hyaluronate | 1.00 |
| Tidecyl Salicylate | 6.00 |
| Salacos HS ® | 2.50 |
| Isostearic Acid | 2.50 |
| Isononyl Isononanoate | 3.75 |
| Hydroxycaprilic Acid | 0.10 |
| Methylparaben | 0.20 |
| Propylparaben | 0.10 |
| Tocopheryl Acetate | 0.55 |
| Phenoxyethanol | 0.20 |
| Deionized Water | Q.S |

EXAMPLE 6

A skin cream (oil in water type) formulation according to the present invention is outlined under Table V.

TABLE V

| INGREDIENT | WEIGHT (%) |
|---|---|
| Hydroxyethylcellulose | 0.50 |
| Magnesium Aluminum Silicate | 0.75 |
| Cocoa Butter | 1.25 |
| Squalene | 1.05 |
| Isostearyl Isononanoate | 2.25 |
| DC Silicone Fluid 200 ® (50 CST) | 1.25 |
| DC Silicone Fluid 200 ® (100 CST) | 0.50 |
| Butylene Glycol | 3.00 |
| Glycerin | 2.50 |
| Sodium Hyaluronate | 0.50 |
| Tridecyl Salicylate | 5.00 |
| Glycereth-7 Hydroxystearate | 1.50 |
| Stearic Acid | 3.50 |
| Cetyl/Stearyl Alcohol | 2.55 |
| Sodium PCA | 2.10 |
| Glyceryl Hydroxystearate | 1.25 |

TABLE V-continued

| INGREDIENT | WEIGHT (%) |
| --- | --- |
| Tocopherol | 0.35 |
| Methylparaben | 0.20 |
| Propylparaben | 0.10 |
| Glydant ® | 0.30 |
| Steareth-20 | 1.20 |
| Disodium EDTA | 0.05 |
| Triethanolamine | 1.50 |
| Deionized Water | Q.S |

EXAMPLE 7

An anhydrous serum formulation according to the present invention is outlined under Table VI.

TABLE VI

| INGREDIENT | WEIGHT (%) |
| --- | --- |
| Sepigel 305 ® | 1.50 |
| SD Alcohol 40 (200°) | 20.00 |
| DC Silicone Fluid 344 ® | QS |
| Squalene | 1.05 |
| Octyl Isononanoate | 2.25 |
| DC Silicone Fluid 200 ® (10 CST) | 5.25 |
| Isononyl Isononanoate | 30.00 |
| Butylene Glycol | 1.00 |
| Tocophenyl Linoleate | 0.50 |
| Propylparaben | 0.10 |
| Tocopheryl Acetate | 0.10 |
| Tridecyl Salicylate | 2.75 |
| Dimethiconol | 2.50 |

EXAMPLE 8

A skin lotion (oil in water type) formulation according to the present inventin is outlined under Table VII.

TABLE VII

| INGREDIENT | WEIGHT (%) |
| --- | --- |
| Xanthan Gum | 0.20 |
| Magnesium Aluminum Silicate | 0.75 |
| Shea Butter Glycerides | 1.25 |
| Squalene | 2.25 |
| Coco Caprylate/Caprate | 3.25 |
| DC Silicone Fluid 200 ® (50 CST) | 0.75 |
| DC Silicone Fluid 200 ® (50 CST) | 0.50 |
| Butylene Glycol | 3.00 |
| Glycerin | 2.00 |
| Sodium Hyaluronate | 0.35 |
| Tridecyl Salicylate | 3.50 |
| Cetyl Alcohol | 1.00 |
| DEA-Cetyl Phosphate | 2.15 |
| Saccharide Isomerate | 1.00 |
| Sodium PCA | 2.10 |
| Sucrose Laurate | 0.50 |
| Ceteth-2 | 0.50 |
| Methylparaben | 0.20 |
| Propylparaben | 0.10 |
| Germall II ® | 0.30 |
| Steareth-20 | 1.20 |
| Tocopheryl Acetate | 0.20 |
| Disodium EDTA | 0.05 |
| Lactic Acid | 0.10 |
| Deionized Water | Q.S |

EXAMPLE 9

A protective skin lotion with sunscreen formulation according to the present invention is outlined under Table VIII.

TABLE VIII

| INGREDIENT | WEIGHT (%) |
| --- | --- |
| Xanthan Gum | 0.15 |
| Seppigel 501 ® | 1.50 |
| Shea Butter | 1.50 |
| Squalene | 2.00 |
| Coco Caprylate/Caprate | 2.25 |
| Propylene Glycol Dicaprylate/Dicaprate | 3.55 |
| DC Silicone Fluid 200 ® (20 CST) | 0.50 |
| DC Silicone Fluid 200 ® (350 CST) | 1.00 |
| Butylene Glycol | 3.00 |
| Glycerin | 1.00 |
| Sodium Hyaluronate | 0.35 |
| Tridecyl Salicylate | 3.00 |
| Cetyl Alcohol | 1.00 |
| DEA-Cetyl Phosphate | 1.25 |
| Parsol MCX ® | 6.00 |
| Benzophenone-3 | 3.00 |
| Ceteth-2 | 0.50 |
| Ceteareth-20 | 1.20 |
| Methylparaben | 0.30 |
| Propylparaben | 0.15 |
| Glydant ® | 0.20 |
| Aloe Vera Gel | 2.00 |
| Tocopheryl Acetate | 0.30 |
| Disodium EDTA | 0.05 |
| Deionized Water | Q.S |

EXAMPLE 10

A clinical study was performed on the composition of Table IX to determine performance of tridecyl salicylate as an anti-aging active.

TABLE IX

| COMPONENT | WEIGHT % |
| --- | --- |
| Silicone 344 Fluid | 15.0 |
| Tridecyl Salicylate | 5.0 |
| Silicone 200/100 Fluid | 5.0 |
| Silicone 1401 Fluid | 5.0 |
| Actiglide Special ® (Bio-hyaluronic Acid) | 5.0 |
| Squalane | 4.0 |
| Butylene Glycol | 3.0 |
| Sepigel 305 ®* | 3.0 |
| Tween 40 ® | 2.5 |
| Germall 115 ® | 0.3 |
| Methylparben | 0.2 |
| Disodium EDTA | 0.1 |
| Deionized Water | qs |

*Isoparaffin dispersion of a polyacrylamide water solution.

Crepey Skin Measurement

The crepey skin protocol is a clinical visual assessment of forearm skin. This condition is associated with photoaged skin and reflects skin which takes on a sagging, rough, wrinkled appearance. The clinical test is 12 weeks in duration and evaluates 2 different test formulations in a paired manner (one on each forearm) using 15 women with moderate forearm crepiness. The study is conducted in a double blinded manner where neither the subject or clinical evaluator has knowledge of the test material being applied to the forearms. Only subjects with equivalent crepiness on both forearms are enrolled.

Assessment

If a formulation is effective it is anticipated that an improvement in forearm crepiness would be observed from baseline. To compare the relative performance of the 2 test formulations, the better formula would show greater/faster improvement in forearm crepiness as compared to the companion formulation. The following "directed-difference" scale is utilized to measure to what extent one formulation is superior to the companion formulation.

- 0=no difference
- 1=slightly better
- 2=moderately bearer
- 3=much better
- 4=dramatically better A directed-difference scale is used to quantitate any perceived difference between right and left treated forearms. If there is no perceivable difference between forearms a 0 is noted. In the event one forearm is better, the more improved forearm is given a score from 1 to 4 (smallest to greatest) where these values represent a difference level of improvement over the companion treated forearm. The forearm which is showing greater improvement will therefore attain a higher average absolute score. One treatment is arbitrarily given a negative assignment while the other is given the positive assignment. In these experiments, the tridecyl salicylate formulations were given a negative assignment whereas the vehicle was given a positive assignment.

Results of the clinical are provided in Table X. They show that the tridecyl salicylate formulation is superior to the vehicle. This is evident as the directed difference scores are in the negative direction favoring the tridecyl salicylate formulation. The only difference between the vehicle and experimental formulations is tridecyl salicylate. All other ingredients, pH, etc. are the same.

TABLE X

| Clinical Anti-Aging Performance | |
| --- | --- |
| 5% Tridecyl Salicylate vs. Vehicle Week | MEAN IMPROVEMENT OVER VEHICLE |
| 0 | 0 |
| 4 | +0.12 |
| 8 | +1.0* |
| 12 | +0.6 |

*Significantly better than vehicle-treated group.

The foregoing description and examples illustrate selected embodiments of the present invention. In light thereof, various modifications will be suggested to one skilled in the art, all of which are within the spirit and purview of this invention.

What is claimed is:

1. A method for treating wrinkling of skin comprising applying to the skin a safe and effective amount of tridecyl salicylate.

* * * * *